(12) United States Patent
Hu et al.

(10) Patent No.: US 11,298,694 B2
(45) Date of Patent: Apr. 12, 2022

(54) ZWITTERION-RUTHENIUM COMPLEX FOR CATALYTIC AEROBIC OXIDATION REACTIONS

(71) Applicant: The Chinese University of Hong Kong, Hong Kong (CN)

(72) Inventors: Rong-Bin Hu, Lanzhou (CN); Ying-Pong Lam, Hong Kong (CN); Wing-Hin Ng, Hong Kong (CN); Ying-Yeung Yeung, Hong Kong (CN); Zhihai Ke, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 17/080,256

(22) Filed: Oct. 26, 2020

(65) Prior Publication Data
US 2021/0121862 A1    Apr. 29, 2021

Related U.S. Application Data

(60) Provisional application No. 62/925,943, filed on Oct. 25, 2019.

(51) Int. Cl.
| | |
|---|---|
| *B01J 31/22* | (2006.01) |
| *B01J 31/18* | (2006.01) |
| *B01J 31/30* | (2006.01) |

(52) U.S. Cl.
CPC ........... *B01J 31/226* (2013.01); *B01J 31/181* (2013.01); *B01J 31/189* (2013.01); *B01J 31/30* (2013.01); *B01J 2531/004* (2013.01); *B01J 2531/821* (2013.01)

(58) Field of Classification Search
None
See application file for complete search history.

(56) References Cited

PUBLICATIONS

Catlow, C.R. et al., "Catalysis making the world a better place", Philosophical Transactions A, 2016, 374:20150089, pp. 1-2, The Royal Society.
Surry, D.S. et al., "Biaryl Phosphane Ligands in Palladium-Catalyzed Amination", Angewandte Chemie Int. Ed. 2008, 47:6338-6361, Wiley-VCH Verlag GmbH & Co. KGaA, Weinheim.
Ruiz-Castillo, P. et al., "Applications of Palladium-Catalyzed C—N Cross-Coupling Reactions", Chemical Reviews, 2016, 116:12564-12649, American Chemical Society.
Ager, D.J. et al., "Asymmetric homogeneous hydrogenations at scale", Chem. Soc. Rev., 2012, 41:3340-3380, The Royal Society of Chemistry.
Alcarazo, M., "Synthesis, Structure, and Applications of α-Cationic Phosphines", Acc. Chem. Res., 2016, 49:1797-1805, American Chemical Society.

(Continued)

*Primary Examiner* — Yun Qian
(74) *Attorney, Agent, or Firm* — Saliwanchik, Lloyd & Eisenschenk (57) ABSTRACT

Zwitterion ligand metal complexes and methods of aerobic oxidation using a zwitterion ligand metal complex are provided. The zwitterion ligand metal complexes can include a transition metal salt and a zwitterion ligand, which can comprise a non-conjugated amide anion-phosphonium cation, an amide anion-ammonium cation, or an iminium cation. The methods of aerobic oxidation can include combining the zwitterion ligand metal complex with an oxidizable compound and molecular oxygen to allow the isolation of an oxidized compound from the oxidizable compound.

8 Claims, 8 Drawing Sheets

(56) References Cited

PUBLICATIONS

Chauvin, R., "Zwitterionic Organometallates", Eur. J. Inorg. Chem., 2000, 577-591, WILEY-VCH Verlag GmbH, D-69451 Weinheim.

Stradiotto, M. et al., "Zwitterionic Relatives of Cationic Platinum Group Metal Complexes: Applications in Stoichiometric and Catalytic δ-Bond Activation", Angew. Chem. Int. Ed., 2010, 49:494-512, Wiley-VCH Verlag GmbH & Co. KGaA, Weinheim.

Weber, P. et al., "A Highly Active Ylide-Functionalized Phosphine for Palladium-Catalyzed Aminations of Aryl Chlorides", Angew. Chem. Int. Ed., 2019, 58:3203-3207, Wiley-VCH Verlag GmbH & Co. KGaA, Weinheim.

Chen, L. et al., "Tri(1-adamantyl)phosphine: Expanding the Boundary of Electron-Releasing Character Available to Organophosphorus Compounds", Journal of the American Chemical Society, 2016, 138:6392-6395, American Chemical Society.

Yamaguchi, K. et al., "Supported Ruthenium Catalyst for the Heterogeneous Oxidation of Alcohols with Molecular Oxygen", Angew. Chem., 2002, 114:4720-4724, Wiley-VCH Verlag GmbH & Co. KGaA, Weinheim.

Alcarazo, M., "α-Cationic Phosphines: Synthesis and Applications", Chem. Eur. J., 2014, 20:7868-7877, Wiley-VCH Verlag GmbH & Co. KGaA, Weinheim.

Ramakrishna, V. et al., "Synthesis of zwitterionic palladium complexes and their application as catalysts in cross-coupling reactions of aryl, heteroaryl and benzyl bromides with organoboron reagents in neat water", Dalton Transactions, 2017, 46:8598-8610, The Royal Society of Chemistry.

Brière, J.F. et al., "Recent advances in cooperative ion pairing in asymmetric organocatalysis", Chem. Soc. Rev., 2012, 41:1696-1707, The Royal Society of Chemistry.

Legros, F. et al., "New Developments in Chiral Cooperative Ion Pairing Organocatalysis by Means of Ammonium Oxyanions and Fluorides: From Protonation to Deprotonation Reactions.", Chem. Rec., 2017, 17:429-440, The Chemical Society of Japan & Wiley-VCH Verlag GmbH & Co. KGaA, Weinheim.

Godemert, J. et al., "Chiral Ammonium Aryloxides: Efficient Multipurpose Basic Organocatalysts", ChemCatChem, 2016, 8:74-85, Wiley-VCH Verlag GmbH & Co. KGaA, Weinheim.

Lee, H. et al., "Zwitterionic Silver Complexes as Carriers for Facilitated-Transport Composite Membranes", Angew. Chem. Int. Ed., 2004, 43:3053-3056, Wiley-VCH Verlag GmbH & Co. KGaA, Weinheim.

Lam, Y.P. et al., "Amide/Iminium Zwitterionic Catalysts for (Trans)esterification: Application in Biodiesel Synthesis", ACS Catalysis, 2019, 9:8083-8092, American Chemical Society.

Journoux-Lapp, C. et al., "Elucidation of the role of betaine hydrochloride in glycerol esterification: towards bio-based ionic building blocks", Green Chemistry, 2017, 19:5647-5652, The Royal Society of Chemistry.

Johnston, R.C. et al., "C—H O non-classical hydrogen bonding in the stereomechanics of organic transformations: theory and recognition", Organic & Biomolecular Chemistry, 2013, 11:5057-5064, The Royal Society of Chemistry.

Berg, L. et al., "The Nature of Activated Non-classical Hydrogen Bonds: A Case Study on Acetylcholinesterase-Ligand Complexes", Chem. Eur. J., 2016, 22:2672-2681, Wiley-VCH Verlag GmbH & Co. KGaA, Weinheim.

Molina, P. et al., "Anion Recognition Strategies Based on Combined Noncovalent Interactions", Chemical Reviews, 2017, 117:9907-9972, American Chemical Society.

Müller, M. et al., "CH-Anion versus anion-π interactions in the crystal and in solution of pentafluorobenzyl phosphonium salts", Dalton Trans., 2010, 39:11329-11334, The Royal Society of Chemistry.

Homs, A. et al., "On the Silver Effect and the Formation of Chloride-Bridged Digold Complexes", Organic Letters, 2013, 15(22):5782-5785, American Chemical Society.

Van Der Vlugt, J.I., "Cooperative Catalysis with First-Row Late Transmission Metals", Eur. J. Inorg. Chem., 2012, pp. 363-375, Wiley-VCH Verlag GmbH & Co. KGaA, Weinheim.

Verhoeven, D.G.A. et al., "Metal-ligand cooperation at tethered π-ligands", Dalton Trans., 2016, 45:15762-15778, The Royal Society of Chemistry.

Grützmacher, H., "Cooperating Ligands in Catalysis", Angew. Chem. Int. Ed., 2008, 47:1814-1818, Wiley-VCH Verlag GmbH & Co. KGaA, Weinheim.

Braunstein, P. et al., "Hemilability of Hybrid Ligands and the Coordination Chemistry of Oxazoline-Based Systems", Angew. Chem. Int. Ed., 2001, 40:680-699, Wiley-VCH Verlag GmbH, D-69451 Weinheim.

Kopylovich, M.N. et al., "Catalytic Oxidation of Alcohols: Recent Advances", Advances in Organometallic Chemistry, 2015, 63:91-174, Elsevier Inc.

Parmeggiani, C. et al., "A step forward towards sustainable aerobic alcohol oxidation: new and revised catalysts based on transition metals on solid supports", Green Chemistry, 2017, 19:2030-2050, The Royal Society of Chemistry.

Remy, H., "Beiträge zur Chemie der Platinmetalle. V. Thermischer Abbau des Ruthentrichlorids und des Ruthendioxyds.", Z. Anorg. Allg. Chem., 1924(137): 365-388, with an English Abstract.

Iles, G.S. et al., "A Thick Film Platinum Resistance Thermometer", Platinum Metals Review, 1975, 19(2):42-47.

Tang, R. et al., "Homogeneous Catalytic Oxidation of Amines and Secondary Alcohols by Molecular Oxygen", J.C.S. Chem. Comm., 1978, p. 562.

Huynh, H.V. et al., "Anion influences on reactivity and NMR spectroscopic features of NHC precursors", RSC Advances, 2018, 8:34960-34966, The Royal Society of Chemistry.

Dijksman, A. et al., "Efficient and Selective Aerobic Oxidation of Alcohols into Aldehydes and Ketones Using Ruthenium/TEMPO as the Catalytic System", J. Am. Chem. Soc., 2001, 123:6826-6833, American Chemical Society.

Guo, H. et al., "Aerobic oxidation of alcohols to aldehydes and ketones using ruthenium(III)/Et$_3$N catalysts", Applied Organometallic Chemistry, 2011, 25:836-842, John Wiley & Sons, Ltd.

Yamaguchi, K. et al., "Efficient Heterogeneous Aerobic Oxidation of Amines by a Supported Ruthenium Catalyst", Angew. Chem. Int. Ed., 2003, 42:1480-1483, Wiley-VCH Verlag GmbH & Co. KGaA, Weinheim.

Yamaguchi, K. et al., "Scope, Kinetics, and Mechanistic Aspects of Aerobic Oxidations Catalyzed by Ruthenium Supported on Alumina", Chem. Eur. J., 2003, 9:4353-4361, Wiley-VCH Verlag GmbH & Co. KGaA, Weinheim.

ZWITTERION-RUTHENIUM COMPLEX FOR CATALYTIC AEROBIC OXIDATION REACTIONS

CROSS-REFERENCE TO RELATED APPLICATION

This application claims the benefit of U.S. Provisional Application Ser. No. 62/925,943, filed Oct. 25, 2019, the disclosure of which is hereby incorporated by reference in its entirety, including all figures, tables and drawings.

BACKGROUND OF THE INVENTION

Catalysis is a core requirement of many chemical processes. Transition metal catalyzed transformations are a major sector in catalysis. Ligands are crucial in dictating the catalytic performance including reactivity, efficiency and even selectivity. Therefore, ligand design and preparation is an ever-growing research area. Efforts directed to the development of novel ligands that demonstrate parameters such as steric and electronic demands of the catalyst centers are readily tuned, which is important for the expansion of scopes and enablement of new reactions. Neutral ligands are most commonly used due to their high accessibility and stability. In recent years, grafting charged moieties to the neutral ligands have emerged as a new approach in ligand modification that fine tune the catalysts' properties and unveil new reactivities. For examples, phosphines and N-heterocyclic carbenes bearing cationic or anionic moieties in conjugation to the ligand systems have been used to enhance catalytic performance.

Zwitterions, which involve site-isolation of the positively and negatively charged partners in the same molecules, are an emerging class of organocatalysts for some reactions, exhibit unusual reactivity and selectivity. Stronger cationic and anionic partners can be achieved if the charge pair is not in conjugation for self-neutralization through charge delocalization. However, non-conjugated zwitterions are not easy prepared, hence their applications as ligands in transition metal catalysis are under-exploited.

Figure 1A:
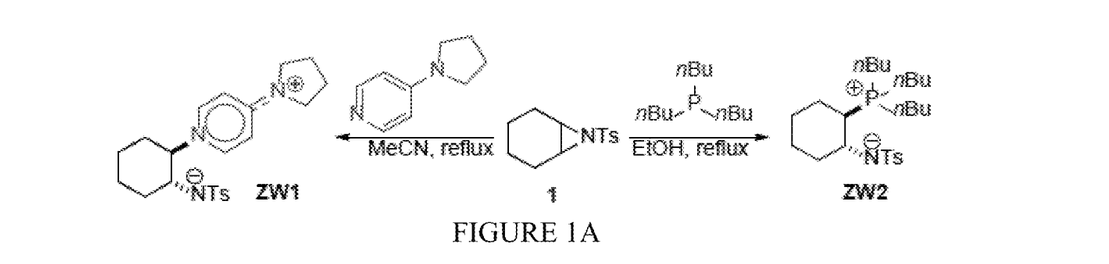
FIG. 1A shows a reaction scheme to form zwitterion ligands ZW1 and ZW2, according to an embodiment of the invention.
Figure 1B:
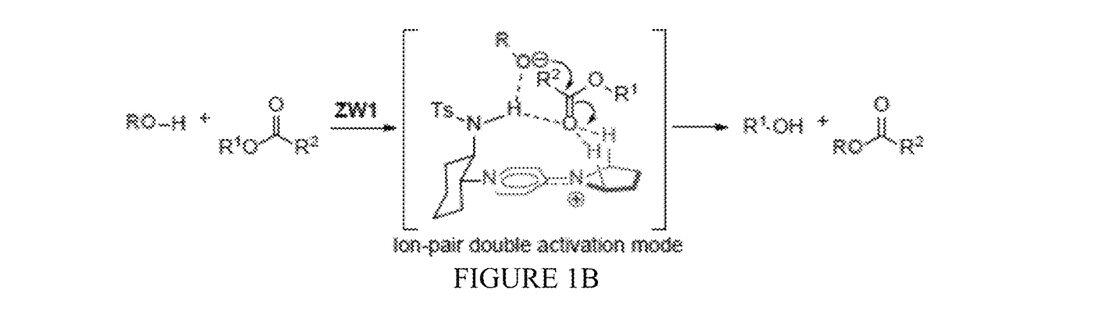
FIG. 1B shows a reaction scheme for transesterification using ZW1 as catalyst.

Recently, a new class of zwitterionic organocatalyst ZW1 based on an iminium cation/amide anion pair was developed, as shown in FIG. 1A, Lam et al. *ACS Catal.* 2019, 9, 8083-8092. ZW1 is readily prepared in one-step by the reaction of aziridine 1 with 4-pyrrolidinopyridine, where the rigid skeleton of ZW1 allows effective site-isolation of the charges. This class of zwitterion catalysts has been successfully applied to (trans)esterification reactions, as shown in FIG. 1B. It was discovered that the charge-pair works synergistically with the pyrrolidinium moiety in zwitterion ZW1 to activate the carbonyl group of an ester through a non-classical hydrogen bond (NCHB) interaction, while the basic sulfonamide anion deprotonates the alcohol. This ability to form a NCHB has not been exploited to form zwitterionic ligand metal complexes with potential as catalysts.

BRIEF SUMMARY OF THE INVENTION

Embodiments of the subject invention provide zwitterion ligand metal complexes and methods of aerobic oxidation using a zwitterion ligand metal complex. The zwitterion ligand metal complexes can include a transition metal salt and a zwitterion ligand. The zwitterion ligand can comprise a non-conjugated amide anion-phosphonium cation, an amide anion-ammonium cation, or an iminium cation. The methods of aerobic oxidation can include combining the zwitterion ligand metal complex with an oxidizable compound and molecular oxygen to allow the isolation of an oxidized compound from the oxidizable compound. The oxidized compound that is isolated can be, for example, an aldehyde or a ketone, though embodiments are not limited thereto.

In an embodiment, a zwitterion ligand metal complex can comprise a transition metal salt and zwitterion ligand comprising a non-conjugated amide anion-phosphonium cation, an amide anion-ammonium cation, or an iminium cation. The amide anion can be, but is not limited to a sulfonic amide, which can be, but is not limited to a toluene sulfonic amide anion. The iminium cation can be, but is not limited to the iminium of 4-pyrrolidinopyridine. The phosphonium cation can be, but is not limited to, a phosphonium ion of a trialkylphosphine. The zwitterion ligand comprising the non-conjugated amide anion-phosphonium cation or amide anion-ammonium or iminium cation can be the ring-opening product of a strained cyclic amide, such as, but not limited to, an aziridine amide. The aziridine amide can be, but is not limited to, a cyclohexene imine amide. The metal salt can be, but is not limited to, a ruthenium (III) salt, for example, but not limited to $RuCl_3$.

In another embodiment, a method of aerobic oxidation using the zwitterion ligand metal complex can comprise combining the zwitterion ligand metal complex with an oxidizable compound and molecular oxygen to allow the isolation of an oxidized compound, such as, but not limited to, an aldehyde or ketone, from the oxidizable compound. The oxidizable compound is a primary alcohol, secondary alcohol, a hydroquinone, an indoline, or 1,2,3,4-tetrahydroquinoxaline. These primary and secondary alcohols include aliphatic alcohols, benzyl alcohols, allyl alcohols, diphenyl methyl alcohols, 1-phenyl allyl alcohols, or 1-alkenyl-allyl alcohols. Any of these primary or secondary alcohols can be substituted with non-aerobic oxidizable substituents at any portion of the alcohol other than the carbon bearing the alcohol functionality. In some cases the primary or secondary alcohols can include a second alcohol that can oxidize to a di-oxidized comprising product, or, depending upon the temperature and stoichiometry with the molecular oxygen allow formation of a mono-oxidized alcohol comprising compound. The molecular oxygen can be provided from air. A solvent (e.g., 1,2-dichloroethane (DCE)) can be used, and the reaction mixture can be heated to temperatures above ambient temperatures, up to or exceeding 100° C. (e.g., in a range of from 23° C. to 100° C. or a range of from 40° C. to 100° C.).

DETAILED DISCLOSURE OF THE INVENTION

Embodiments of the subject invention provide zwitterion ligand metal complexes and methods of aerobic oxidation using a zwitterion ligand metal complex. The zwitterion ligand metal complexes can include a transition metal salt and a zwitterion ligand, which can comprise a non-conjugated amide anion-phosphonium cation, an amide anion-ammonium cation, or an iminium cation. The methods of aerobic oxidation can include combining the zwitterion ligand metal complex with an oxidizable compound and molecular oxygen to allow the isolation of an oxidized compound from the oxidizable compound. The oxidized compound that is isolated can be, for example, an aldehyde or a ketone, though embodiments are not limited thereto.

Figure 1C:
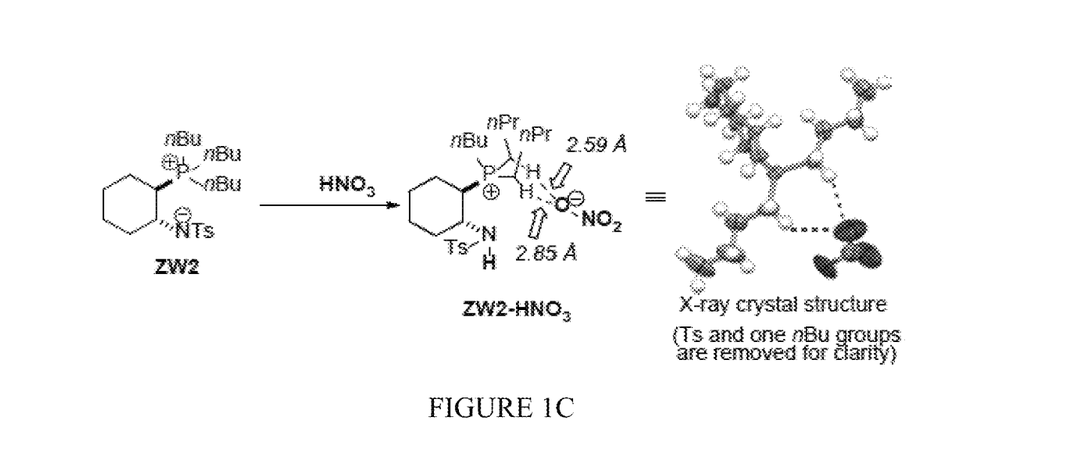
FIG. 1C shows a reaction scheme formation of nitric acid protonation of ZW2 and the x-ray structure of the protonated species $ZW2-HNO_3$.
Figure 2:
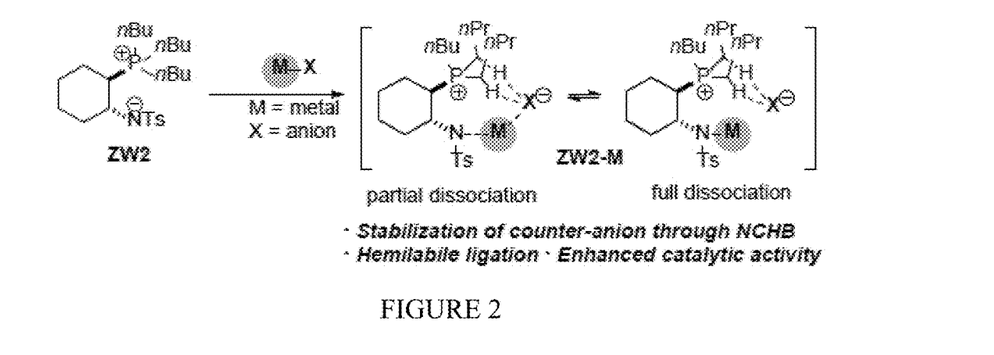
FIG. 2 shows a reaction scheme for the formation of a metal complex with ZW2, according to an embodiment of the invention.

In addition to the pyridinium ligand ZW1, a phosphonium zwitterion ligand, ZW2, according to an embodiment of the subject invention, can be prepared by reacting tri-n-butylphosphine with aziridine 1, as shown in FIG. 1A. ZW2 is air/moisture stable and its preparation is readily scalable. Similar to the non-classical hydrogen bond (NCHB) in ZW1, the nitrate anion interacts with the phosphonium cationic moiety in a salt formed between $HNO_3$ and ZW2, $ZW2-HNO_3$, where, as characterized by X-ray crystallography, forms a NCHB, as shown in FIG. 1C. In an embodiment, a zwitterion ligand, such as but not limited to ZW2, is capable of forming a complex with one or more transition metal salts M-X to form charge-neutral metal complexes, such as ZW2-M, as shown in FIG. 2. The complex displays an amide anion coordinated to the metal center with dissociation of the counter-anion X from the metal center by NCHB formation with the phosphonium cationic moiety, as shown in FIG. 2. Dissociation of the basic counter-anion X enhances the reactivity of the metal center. Rather than employing a common approach where silver salts are used to remove the metal's counter-anion(s) irreversibly, according to embodiments of the invention, the counter-anion X remains in the putative zwitterion-metal complex ZW2-M in close proximity to the metal center. Thus, the amide and the phosphonium/X moieties are situated to synergistically form a bifunctional ligand whiles the counter-anion X reversibly coordinates to and dissociate from the metal center. This hemilabile interaction allows the ligands to modify the binding mode and stabilize reactive intermediates along the reaction pathway, which enhances catalytic performance in various reactions.

Figure 3A:
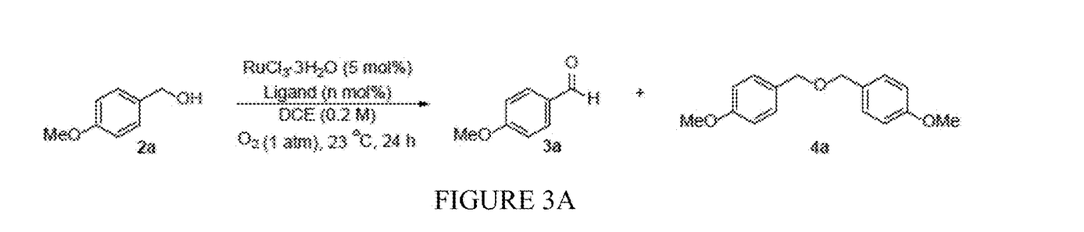
FIG. 3A shows a reaction scheme for the aerobic oxidation of p-methoxy benzyl alcohol using a ruthenium(III) chloride ligand catalyst.
Figure 3B:
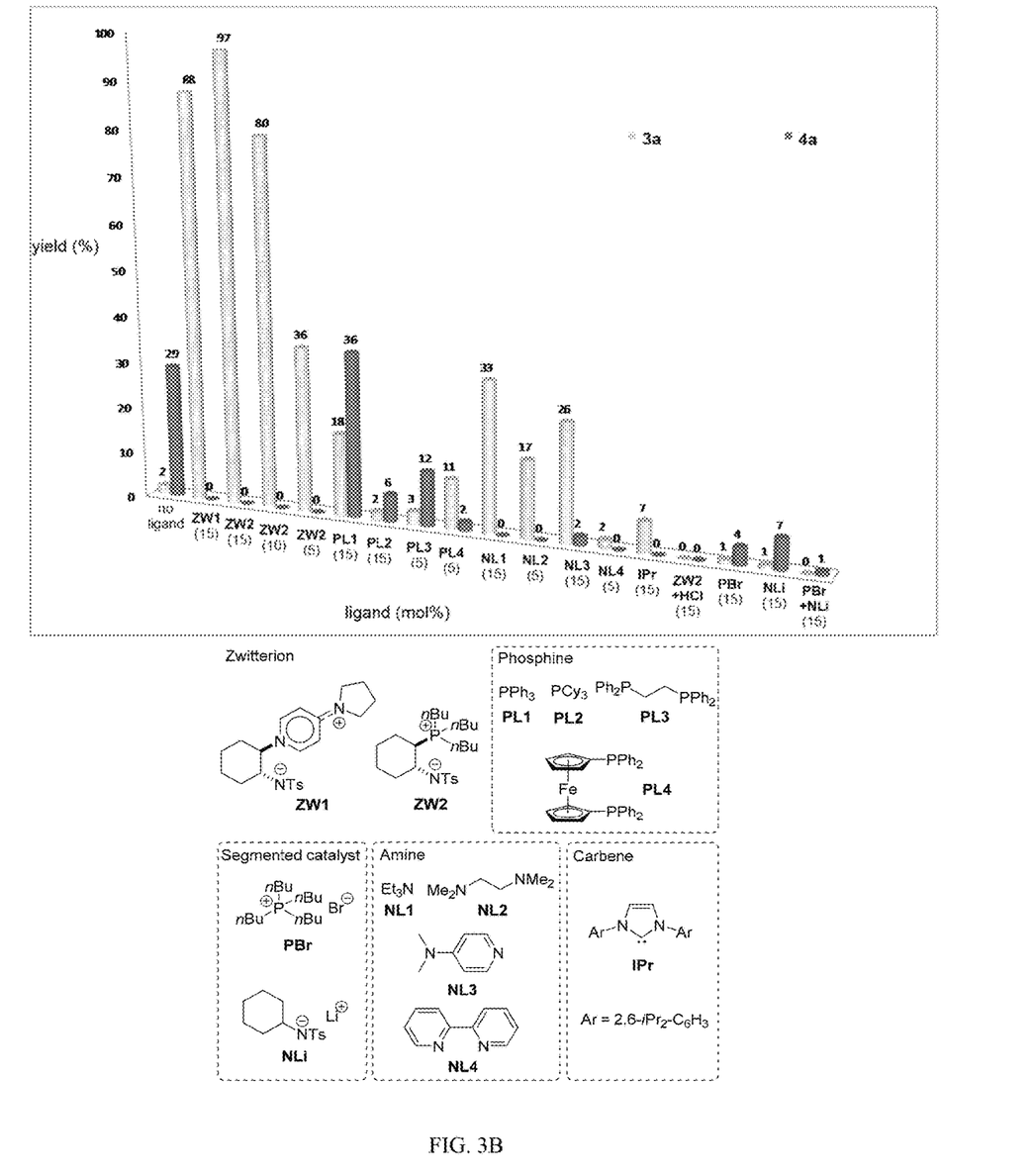
FIG. 3B shows a bar graph for the yield and selectivity of the oxidation of FIG. 3A with $RuCl_3 \cdot 3H_2O$ with various ligands indicated below.

To demonstrate this behavior, the oxidation of alcohols to carbonyls can be performed, as shown in FIG. 3A. The transformation is a ubiquitous and pivotal reaction in research and industry, and important for the formation of carbonyl compounds as medicines, agricultural chemicals, and fragrances. Molecular oxygen at 1 atmosphere (atm) can be used as the oxidant, which is highly desired in industrial processes because water is the only by-product. This type of reaction has been studied using various tailor-made transition metal complexes. Oxidation of alcohol 2a to aldehyde 3a at room temperature using ruthenium trichloride as a catalyst is sluggish when conducted in the absence of external ligand, unless high pressure and temperature are employed. The formation of an ether side product, 4a, predominates, as indicated in FIG. 3B. In contrast, the oxidation proceeds smoothly when zwitterion ZW1 is added as the external ligand, according to an embodiment of the invention. The performance is further enhanced when the phosphonium zwitterion ZW2 is used as the ligand in otherwise identical conditions, giving the desired aldehyde 3a in 97% yield, with no formation of an ether side product 4a. A 3:1 ratio of ligand and Ru (ligand:Ru) provides optimal catalytic activity. Comparing with many other common charge-neutral ligands such as phosphines PL1-PL4, amines NL1-NL4, and N-heterocyclic carbene IPr, the catalytic performance using zwitterionic ligand ZW2 is far superior. Note that the HCl salt of ZW2 performs the reaction but only sluggishly, indicating the importance of the basic amide anion in the coordination to the metal center for the catalytic oxidation reaction. Phosphonium salt PBr and tosyl amide NLi, which are the segmented catalysts of ZW2, allow a sluggish reaction individually or when these components are employed in a 1:1 mixture as the ligand, which points to the synergistic effect of the site-isolated phosphonium and amide moieties of ZW2 to form the active Ru catalyst.

Figure 4A:
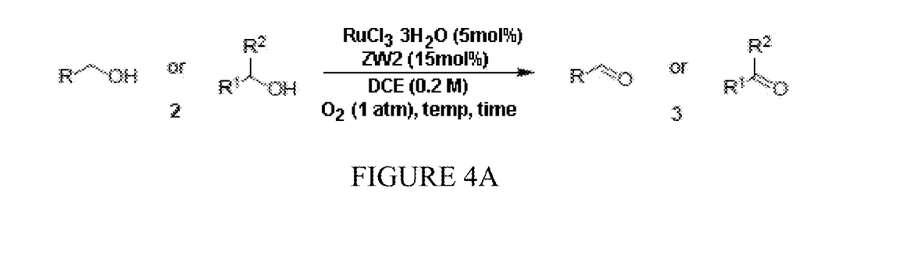
FIG. 4A shows a reaction scheme for the aerobic oxidation of primary and secondary alcohols using a Ru(III)-ZW2 catalyst, according to an embodiment of the invention.
Figure 4B:
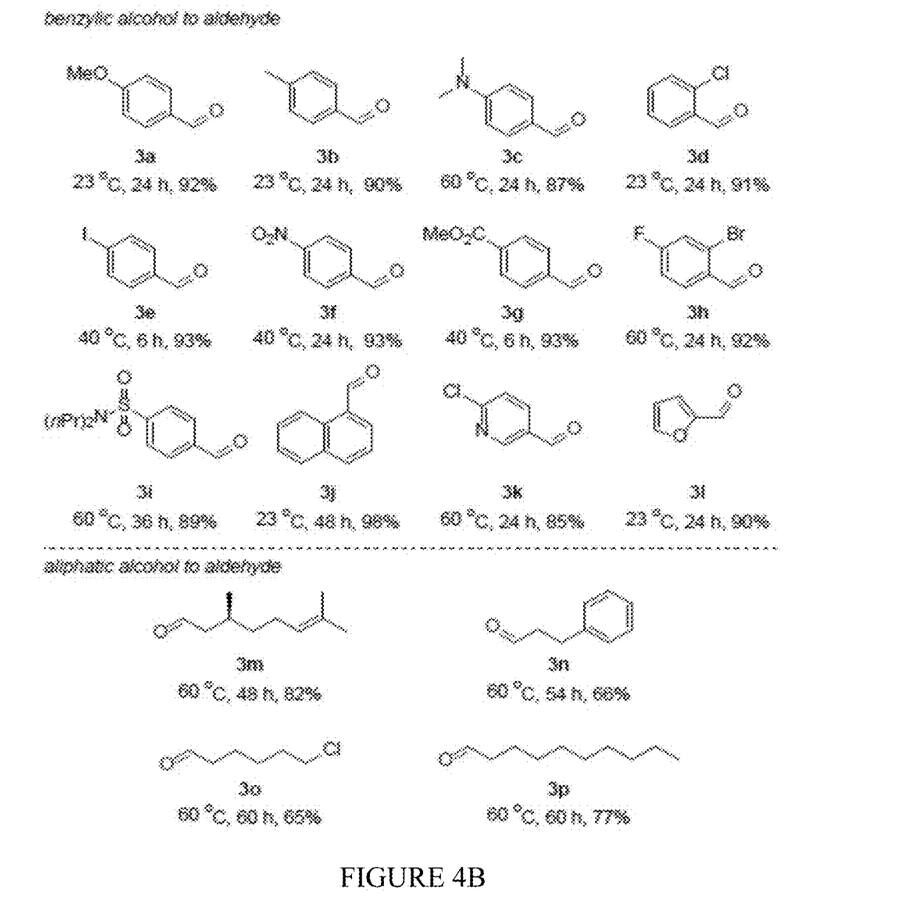
FIG. 4B shows the structure of aldehydes for the aerobic oxidation of primary alcohols as shown in FIG. 4A to various benzyl aldehydes and aliphatic aldehydes, according to an embodiment of the invention.

The catalytic performance of the zwitterionic ruthenium complex facilely oxidizes a broad scope of alcohol substrates, as shown in FIG. 4A. Benzyl alcohols with electron-donating (methyl, methoxy, and dimethylamine) or electron-withdrawing (chloro, bromo, iodo, nitro, methyl ester, and sulfonamide) substituents successfully oxidize to the corresponding aldehydes in good yields (3a-3l), as indicated in FIG. 4B. Alcohols with naphthyl, pyridinyl and furanyl substituents are compatible with the catalytic protocol (3j-3l). Aliphatic primary alcohols result in the desired aldehydes smoothly (3m-3p), as indicated in FIG. 4B. Notably, the olefin functionality in substrate 3m remained intact under the mild and oxidative reaction conditions.

Figure 4C:
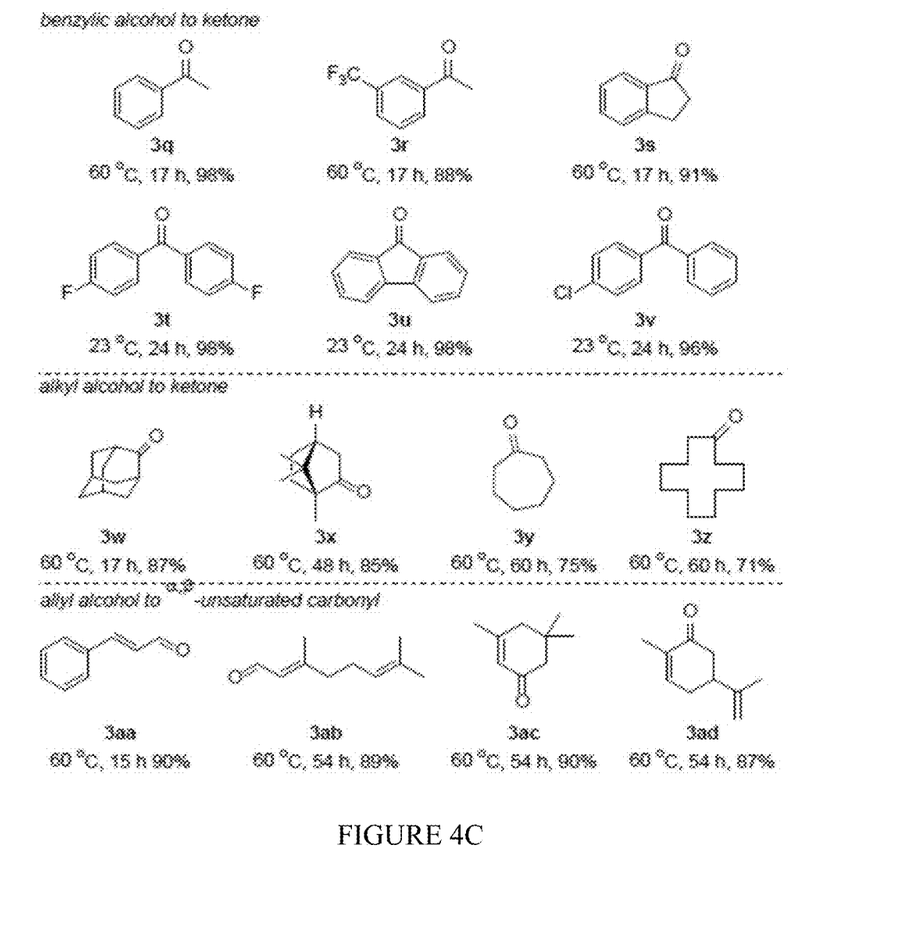
FIG. 4C shows the structure of ketones and aldehydes for the aerobic oxidation of secondary alcohols and allyl alcohols, respectively as shown in FIG. 4A to various benzyl ketones and aliphatic ketones, and $\alpha,\beta$-unsaturated aldehydes, according to an embodiment of the invention.

As indicated in FIG. 4C, various secondary alcohols 2q-2z resulting in the desired aryl and alkyl substituted ketones 3q-3z. Reaction temperature can be increased to compensate for the inherently slower reaction of the secondary alcohol substrates. The zwitterion ligand metal complex catalytic is compatible with the oxidation of allylic alcohols 2aa-2ad, giving the corresponding α,β-unsaturated carbonyl compounds 3aa-3ad.

Figure 5A:
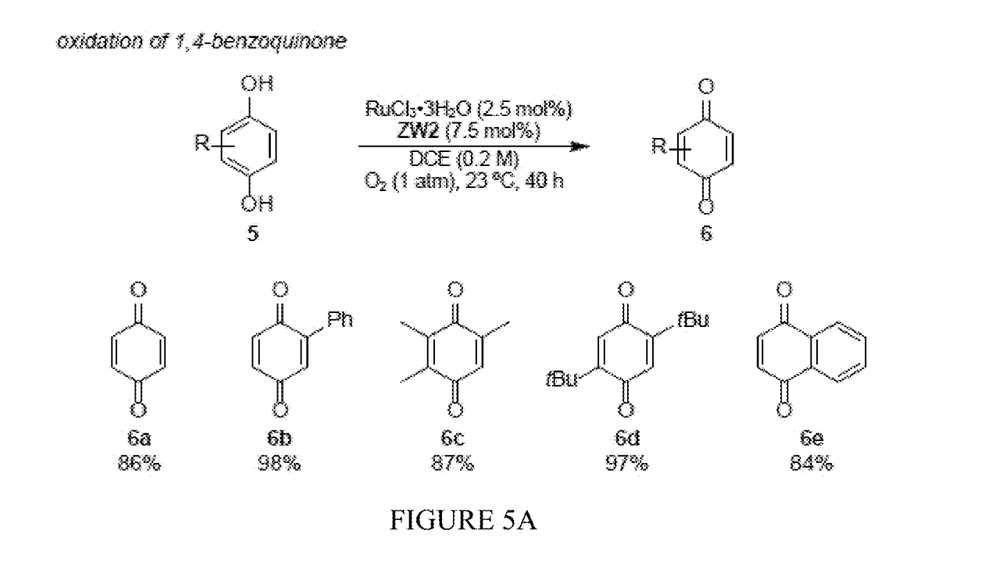
FIG. 5A is a reaction scheme for the aerobic oxidation of 1,4-hydroquinones to 1,4-benzoquinones using a Ru(III)-ZW2 catalyst, according to an embodiment of the invention.
Figure 5B:
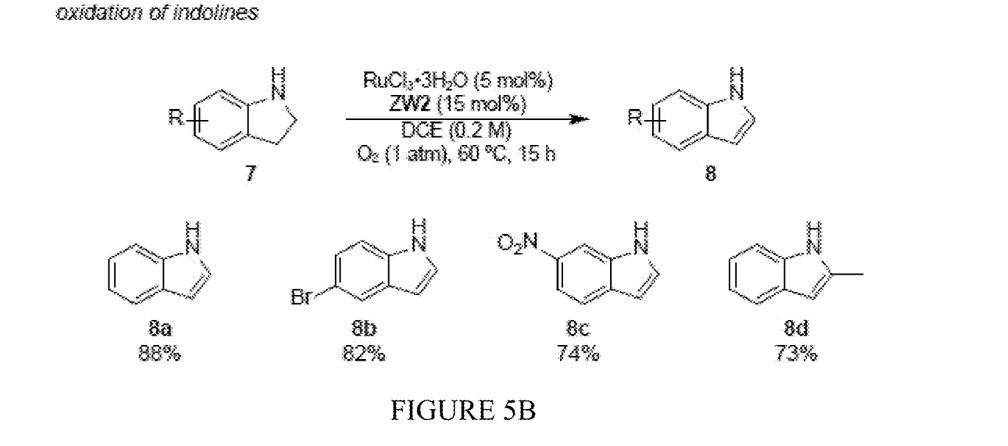
FIG. 5B is a reaction scheme for the aerobic oxidation of indolines to indoles using a Ru(III)-ZW2 catalyst, according to an embodiment of the invention.
Figure 5C:
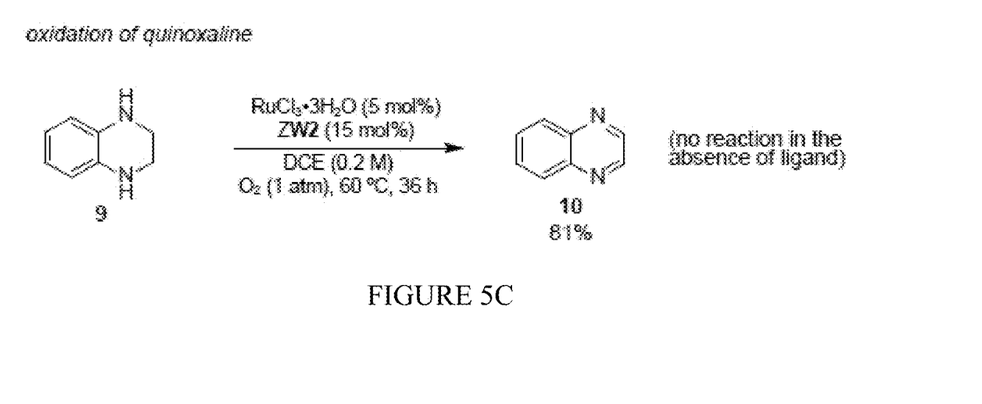
FIG. 5C is a reaction scheme for the aerobic oxidation of 1,2,3,4-tetrahydroquinoxaline to quinoxaline using a Ru(III)-ZW2 catalyst, according to an embodiment of the invention.

Referring to FIG. 5A, in an embodiment, hydroquinone 5a can undergo oxidative dehydrogenation to yield 1,4-benzoquinone 6a in 86% yield using 2.5 mol % of Ru catalyst complex. Substituted hydroquinones 5b-5d are converted into 1,4-benzoquinones 6b-6d in excellent yields, and 1,4-naphthoquinone 6e is formed from 1,4-dihydroxylnaphthalene 5e. In another embodiment of the invention, as indicated in FIG. 5B, the oxidative dehydrogenation of indolines 7 to indoles 8 is readily carried out. Quinoxaline 10 was also obtained through the double oxidation of 1,2,3,4-tetrahydroquinoxaline 9, as shown in FIG. 5C.

Figure 6:
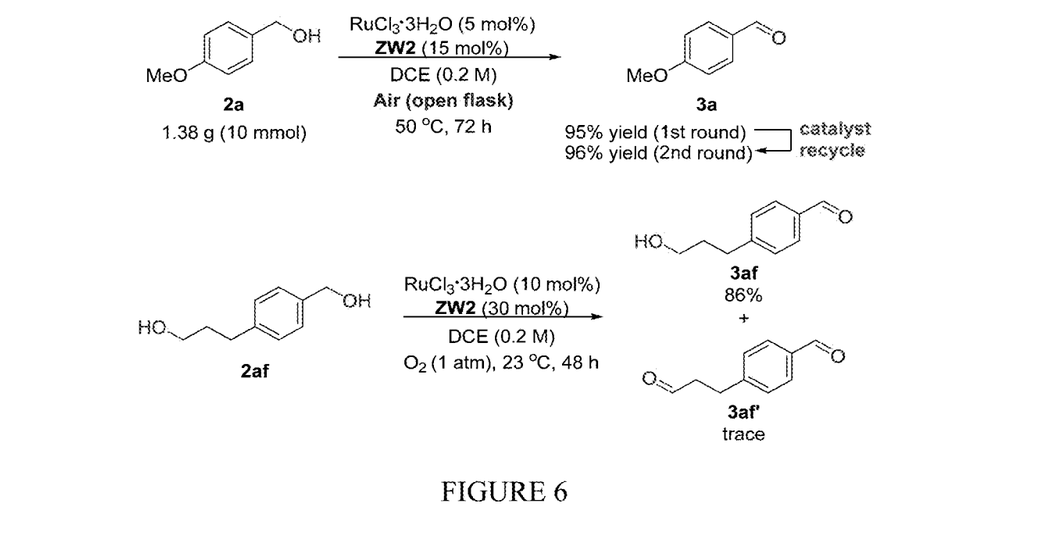
FIG. 6 shows reaction schemes for the aerobic oxidation of p-methoxy benzyl alcohol using a Ru(III)-ZW2 catalyst, according to an embodiment of the invention, with air as the source of oxygen and the selectivity for the oxidation of a benzyl alcohol over an aliphatic alcohol.

The practicality of the oxidation can be demonstrated by conducting the reaction under ambient air at gram-scale, as shown in FIG. 6. The temperature was increased to compensate the reduced reaction rate due to the lower concentration of molecular oxygen. The oxidation reaction of 2a proceeds smoothly to give aldehyde 3a in 95% yield under the optimal conditions. In addition, the catalyst complex can be recovered simply by precipitation and the recycled catalyst promotes the same reaction without observable loss of catalytic performance. The catalytic protocol could also be applied to the chemoselective oxidation of diol 2af and the mono-oxidized product 3af was obtained exclusively.

Figure 7:
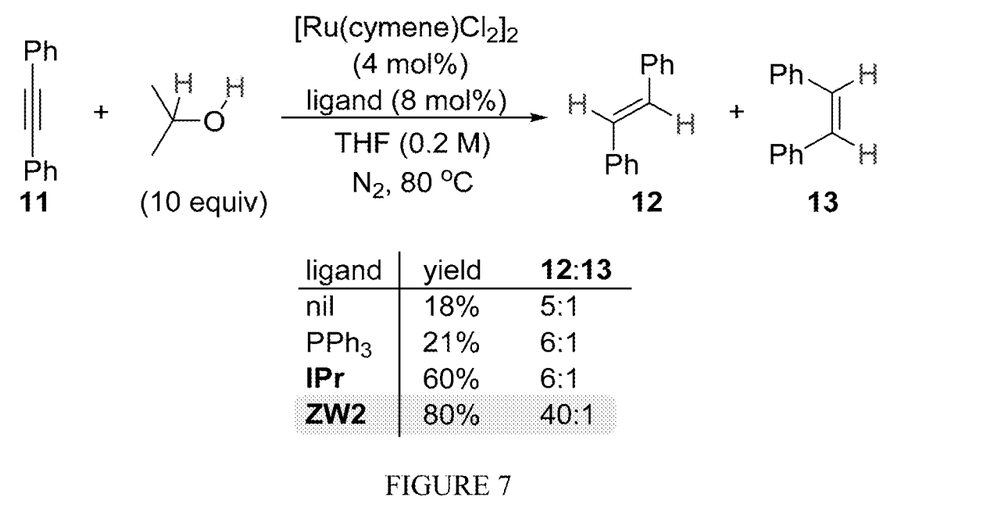
FIG. 7 is a reaction scheme for a stereoselective transfer semi-hydrogenation reaction.

FIG. 7 is a reaction scheme for a stereoselective transfer semi-hydrogenation reaction. Referring to FIG. 7, using Ru(II) (low valence metal to stabilize the hydride) together with the ZW2 ligand effectively catalyzes the transfer semi-hydrogenation of diphenylacetylene (11) into trans-1,2-diphenylethylene (12), with a yield of at least 80%. Even more advantageously, excellent stereoselectivity (12:13=40:1) can be obtained and was observed. In contrast, ligands such as triphenylphosphine and NHC carbene IPr gave only moderate yield and stereoselectivity.

Materials and Methods

The aerobic oxidation reactions for FIGS. 4A-C were conducted with 2 (0.3 mmol), $RuCl_3 \cdot 3H_2O$ (5 mol %), ZW2 (15 mol %) in DCE (1.5 mL) in a sealed tube (10 mL capacity) under $O_2$ (1 atm) at the indicated times and temperatures and with the isolated yields provided under the product structures.

The aerobic oxidation reactions for FIGS. 5A-C were conducted with substrate (0.3 mmol), $RuCl_3 \cdot 3H_2O$ (n mol %), ZW2 (3×n mol %) in DCE (1.5 mL) in a sealed tube (10 mL capacity) under $O_2$ (1 atm) with the isolated yields provided under the product structures.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:
1. A zwitterion ligand metal complex, comprising:
a transition metal salt; and
a zwitterion ligand of the structure:

2. The zwitterion ligand metal complex according to claim 1, wherein the metal salt is a ruthenium (III) salt.

3. The zwitterion ligand metal complex according to claim 2, wherein the ruthenium (III) salt is $RuCl_3$.

4. A method of aerobic oxidation, comprising:
providing the zwitterion ligand metal complex according to claim 1;
providing oxidizable compound;
providing molecular oxygen;
combining the zwitterion ligand metal complex, the oxidizable compound, and the molecular oxygen to produce an oxidized compound; and
isolating the oxidized compound from the oxidizable compound.

5. The method according to claim 4, wherein the oxidizable compound is a primary alcohol, secondary alcohol, a hydroquinone, an indoline, or 1,2,3,4-tetrahydroquinoxaline, wherein the primal), alcohol is an aliphatic alcohol, a benzyl alcohol, or an allyl alcohol, wherein the secondary alcohol is an aliphatic alcohol, a benzyl alcohol, an allyl alcohol, a diphenyl methyl alcohol, a 1-phenyl allyl alcohol, or a 1-alkenyl-allyl alcohol, and wherein the oxidized compound is an aldehyde or a ketone.

6. The method according to claim 4, further comprising:
providing a solvent; and
combining the solvent with the zwitterion ligand metal complex, the oxidizable compound, and the molecular oxygen.

7. The method according to claim 6, wherein the solvent is 1,2-dichloroethane (DCE), and wherein providing molecular oxygen comprises providing air.

8. The method according to claim 4, further comprising heating to a temperature in a range of from 23° C. to 100° C.

* * * * *